(12) United States Patent
Metlitz et al.

(10) Patent No.: US 11,647,738 B2
(45) Date of Patent: May 16, 2023

(54) VOLUMETRIC PUPAE DISPENSER

(71) Applicant: Verily Life Sciences LLC, South San Francisco, CA (US)

(72) Inventors: Matthew Metlitz, Menlo Park, CA (US); Peter Massaro, San Carlos, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 174 days.

(21) Appl. No.: 16/872,788

(22) Filed: May 12, 2020

(65) Prior Publication Data

US 2020/0375162 A1    Dec. 3, 2020

Related U.S. Application Data

(60) Provisional application No. 62/854,396, filed on May 30, 2019.

(51) Int. Cl.
| | | |
|---|---|---|
| *A01K 67/033* | (2006.01) | |
| *A01K 29/00* | (2006.01) | |
| *G06Q 50/02* | (2012.01) | |

(52) U.S. Cl.
CPC ............ *A01K 67/033* (2013.01); *A01K 29/00* (2013.01); *A01K 2227/706* (2013.01); *G06Q 50/02* (2013.01)

(58) Field of Classification Search
CPC .... A01K 29/00; A01K 29/005; A01K 67/033; A01K 2227/706
See application file for complete search history.

(56) References Cited

U.S. PATENT DOCUMENTS 5,074,247 A * 12/1991 Gupta ................... A01K 1/031
                                                              119/6.5
5,178,094 A *  1/1993 Carr ...................... A01K 67/033
                                                              119/6.5
(Continued)

FOREIGN PATENT DOCUMENTS

| CN | 1261866 | 6/2006 |
| CN | 107176336 | 9/2017 |

(Continued)

OTHER PUBLICATIONS

International Application No. PCT/US2020/033522, International Search Report and Written Opinion, dated Sep. 17, 2020, 12 pages.

*Primary Examiner* — Monica L Perry
*Assistant Examiner* — Aaron M Rodziwicz
(74) *Attorney, Agent, or Firm* — Kilpatrick Townsend & Stockton LLP

(57) ABSTRACT

A device comprising a dispenser assembly comprising a frame having a first surface and a second surface, wherein the frame defines a pathway to enable movement of a moveable member within the frame, an inlet opening in the first surface of the frame and a drain opening in the second surface of the frame, the inlet opening and the drain opening providing access to the pathway, wherein the frame further comprises a filter overlaying the drain opening; and a moveable member translatable within the pathway between a first position and a second position, the moveable member defining at least one bore, wherein at least one of the at least one bore is aligned with the inlet opening at the first position; and a reservoir container coupled to the dispenser assembly, the reservoir container defining a dispensing opening, the dispensing opening aligned with the inlet opening of the frame.

35 Claims, 9 Drawing Sheets

(56) References Cited

U.S. PATENT DOCUMENTS

| | | | |
|---|---|---|---|
| 5,594,654 A | 1/1997 | Shuman et al. | |
| 8,733,284 B2* | 5/2014 | Courtright | A01K 29/00 |
| | | | 119/6.6 |
| 9,510,572 B2* | 12/2016 | Aldana | A01K 67/033 |
| 9,642,344 B2* | 5/2017 | Unger | A01K 67/033 |
| 11,291,190 B1* | 4/2022 | Peeters | A01K 67/033 |
| 2012/0060446 A1* | 3/2012 | Merz | B65B 37/20 |
| | | | 53/167 |
| 2013/0319334 A1* | 12/2013 | Newton | A01K 67/033 |
| | | | 119/51.01 |

FOREIGN PATENT DOCUMENTS

| | | | |
|---|---|---|---|
| CN | 107176336 A | * | 9/2017 |
| DE | 29623207 | | 4/1998 |

\* cited by examiner

VOLUMETRIC PUPAE DISPENSER

CROSS-REFERENCE TO RELATED APPLICATIONS

This application claims priority to U.S. Provisional Patent Application No. 62/854,396, titled "Volumetric Pupae Dispenser" filed on May 30, 2019, the entirety of which is hereby incorporated by reference.

FIELD

The present disclosure relates generally to the mass-rearing of insects. More specifically, but not by way of limitation, this disclosure relates to devices and methods for dispensing insect pupae.

BACKGROUND

Insect pupae in a mass-rearing environment, such as a sterile insect technique (SIT) program, involves rearing large numbers of insects from eggs and may involve releasing them into the wild. Maintaining an effective rearing program can be difficult, including maintaining a high yield and detecting problems during the rearing process. For example, clean environments and effective feeding routines may be of significant importance, as well as safe handling of the insects during the rearing process.

SUMMARY

Various examples are described for devices and methods for dispensing insect pupae. One example device includes a dispenser assembly comprising: a frame having a first surface and a second surface opposite the first surface, wherein the frame defines: a pathway to enable movement of a moveable member within the frame, an inlet opening in the first surface of the frame, the inlet opening providing access to the pathway, and a drain opening in the second surface of the frame, the drain opening providing access to the pathway, wherein the frame further comprises a filter overlaying the drain opening; and a moveable member translatable within the pathway between a first position and a second position, the moveable member defining at least one bore oriented perpendicular to the pathway, wherein: when the moveable member is at the first position, the bore is aligned with the inlet opening; and a reservoir container coupled to the dispenser assembly, the reservoir container defining a dispensing opening at a first end of the reservoir container, the dispensing opening aligned with the inlet opening of the frame.

One example method includes providing a device comprising: a dispenser assembly comprising: a frame having a first surface and a second surface opposite the first surface, wherein the frame defines: a pathway to enable movement of a moveable member within the frame, an inlet opening in the first surface of the frame, the inlet opening providing access to the pathway, and a drain opening in the second surface of the frame, the drain opening providing access to the pathway, wherein the frame further comprises a filter overlaying the drain opening; a moveable member translatable within the pathway between a first position and a second position, the moveable member defining at least one bore oriented perpendicular to the pathway, wherein: when the moveable member is at the first position, the bore is aligned with the inlet opening, and a reservoir container coupled to the dispenser assembly, the reservoir container defining a dispensing opening at a first end of the reservoir container, the dispensing opening aligned with the inlet opening of the frame; receiving a mixture of a liquid and a plurality of insect pupae or insect larvae into the reservoir container; straining the mixture using the filter overlaying the drain opening; moving the moveable member between the first position and the second position using an actuator; and outputting the plurality of insect pupae or insect larvae from the bore.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Figure 1:
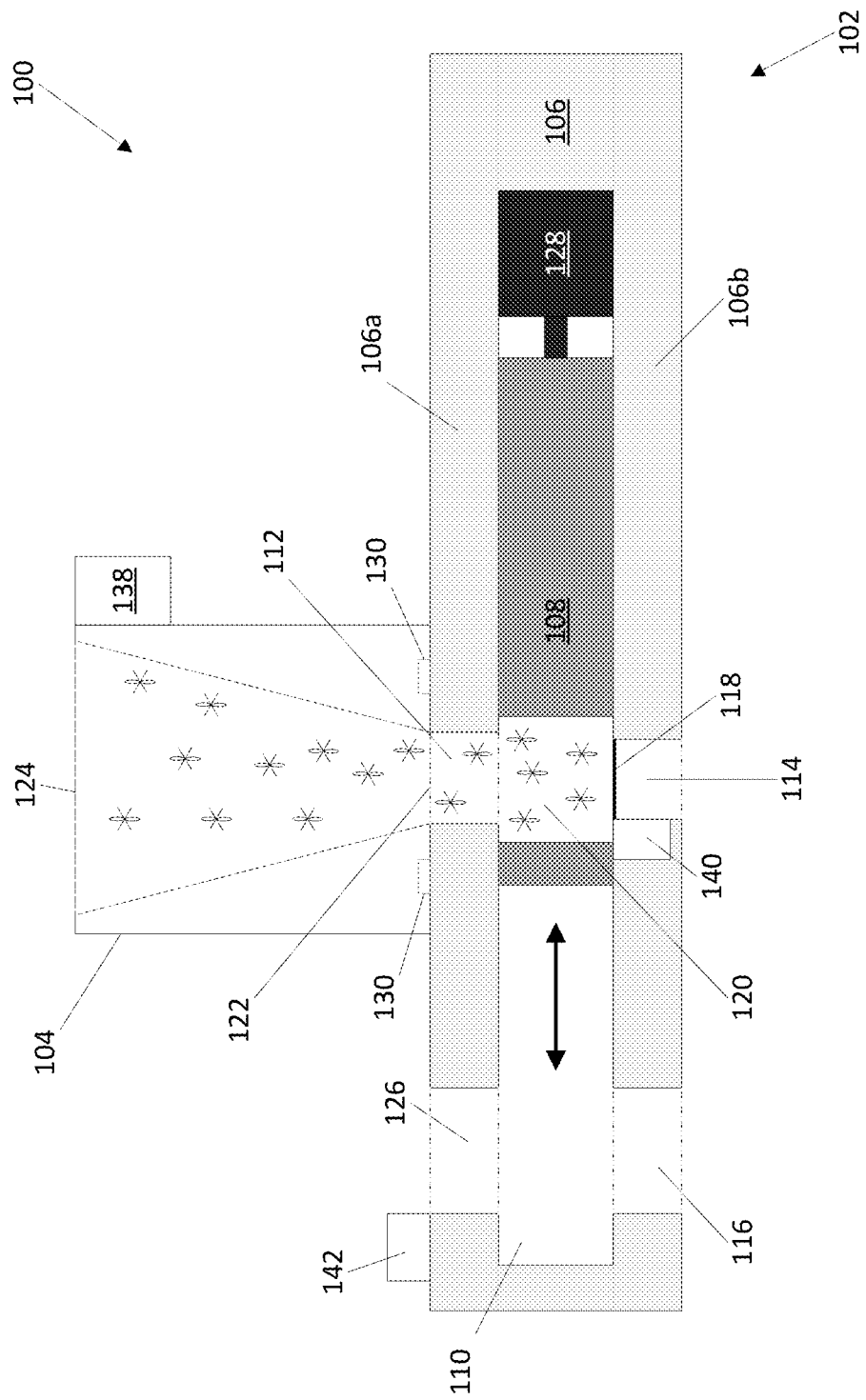
FIGS. 1-7 show example devices for dispensing insect pupae according to this disclosure.

Examples are described herein in the context of devices and methods for dispensing insect pupae. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

When mass rearing insects, it is important to dose the correct number of pupae into a container to ensure the maximization of the mating and egg production process. As such, there needs to be an accurate method for counting the insect pupae. However, manual methods of dosing and counting insect pupae can be very time and labor intensive. Particularly, counting and dispensing known amounts of pupae by manually counting the individual pupa, e.g., using a pipette, is extremely time consuming and tedious. Counting and dispensing known amounts of pupae by transferring the pupae into containers and estimating the number inside the container can result in an inaccurate count and still requires a significant amount of labor.

When mass rearing insects, it may be desirable to dispense a dose of insect pupae (or simply "pupae") without the need for manual counting and measurement by a user. Examples according to this disclosure can provide for the dispensing of insect pupae through the use of a semi-automated or fully automated device and method. While the examples and description below describe the dispensing of insect pupae, insect larvae or any other life-stage of an insect may be dispensed as described below.

In an illustrative example, a mixture of mosquito pupae and the liquid (e.g., water) that the pupae are being carried in are introduced into a pupae dosing device. A dose refers to a substantially consistent quantity of pupae taken from a population of pupae. Thus, this example pupae dosing device will obtain, over multiple iterations, a substantially constant number of pupae from a pupae population and dispense them, such as into individual containers per dose.

This example device includes a reservoir that collects the pupae and the liquid, a moveable member with a bore extending through the moveable member that aligns with a dispensing opening in the reservoir. The device also includes a filter (e.g., mesh) located underneath the bore, while the moveable member's bore is aligned with the reservoir's opening, that permits the liquid to drain from the bore while holding the pupae within the bore. The device also defines an output opening at a different location than the filter. The moveable member moves back and forth between the two locations to receive the pupae and liquid from the reservoir, drain the fluid through the filter, and then dispense the pupae through the output opening.

The reservoir holds the mosquito pupae and the liquid and allows liquid and pupae to exit through its opening, when the bore in the moveable member is aligned with it. The mosquito pupae and the liquid flow through the dispensing opening and into the bore in the moveable member. As the mosquito pupae and the liquid flow into the bore, the liquid continues to flow through the filter and drains from the bore while the mosquito pupae are caught and contained in the bore. The liquid will drain until a saturation point occurs where the pupae fill substantially the entire volume of the bore, thereby clogging any holes in the filter. When the device reaches this saturation point, the number of pupae within the bore is substantially fixed based on the size of the bore.

In this example, after the device reaches the saturation point, an actuator moves the moveable member along a pathway until the bore is aligned with the output opening. A solid portion of the moveable member that does not have a bore extending through it will then block the opening in the reservoir so that any of the pupae and/or liquid remaining in the reservoir are not able to flow out of the reservoir.

The actuator moves the moveable member until the bore is aligned with the output opening. At which time, gravity, a water rinse, or both will cause the pupae to fall through the output opening and into a container positioned underneath the output opening to catch the pupae. Once the pupae are dispensed from the bore, the actuator will move the moveable member back to the original position where the bore is aligned with the reservoir's drain. The process is then repeated to dispense another dose of mosquito pupae.

By using this pupae dosing device, each dose of pupae has substantially the same number of pupae based on the bore size selected for the moveable member. By using such a technique, the dispensing system provides a more accurate and consistent count of the pupae than when an individual would manually measure the pupae using a cup. In addition, the device operates much more quickly than manual pupae dispensing. Thus the pupae dosing device provides a faster, more accurate, and less labor-intensive method for dosing the pupae than by manually counting the individual pupae using a pipette. Incorporating the actuator into the pupae dosing device permits the device to be partially or fully automated in order to reduce or eliminate the need for human operation of the pupae dosing device.

This illustrative example is given to introduce the reader to the general subject matter discussed herein and the disclosure is not limited to this example. The following sections describe various additional non-limiting examples and examples of systems and methods for dispensing insect pupae.

Referring now to FIG. 1, FIG. 1 shows an example device 100 for dispensing insect pupae. In this example, the device 100 is made out of homopolymer acetal (e.g., Delrin®); however, it may be made out of any suitable material or materials such as copolymer acetal, acrylic, metal, plastic, etc. The device 100 includes a dispenser assembly 102 and a reservoir container 104.

Figure 2:
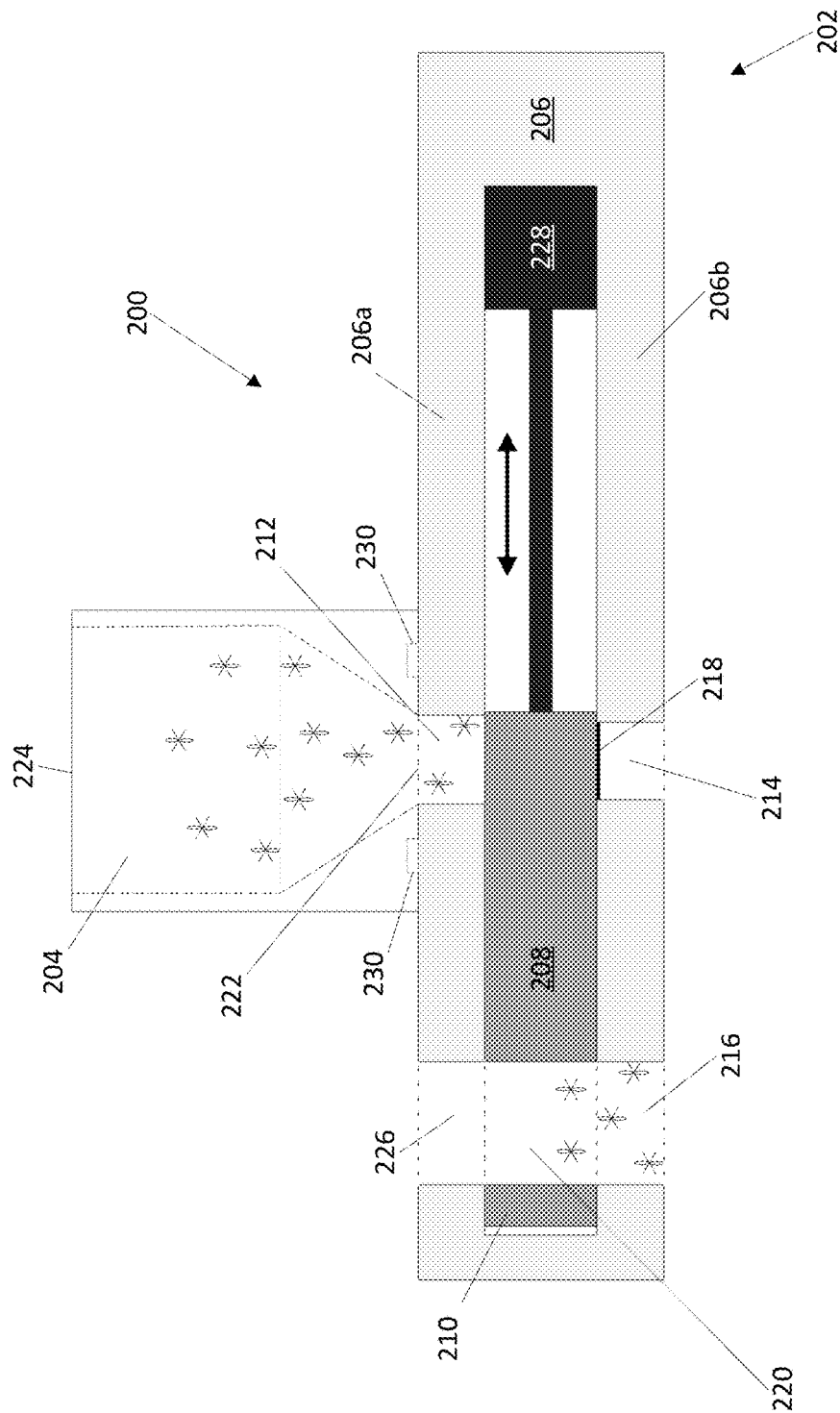
Figure 3:
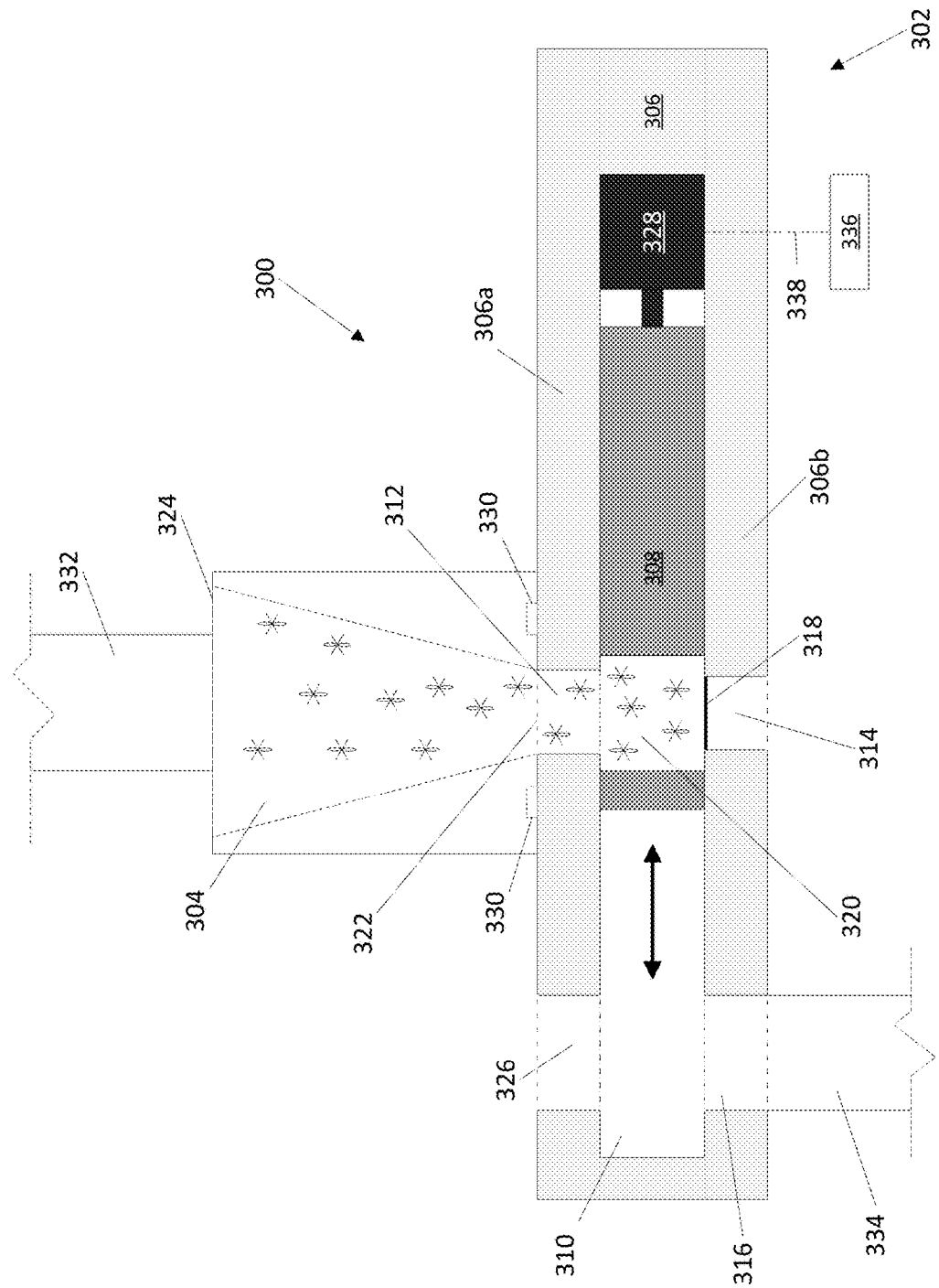
Figure 6:
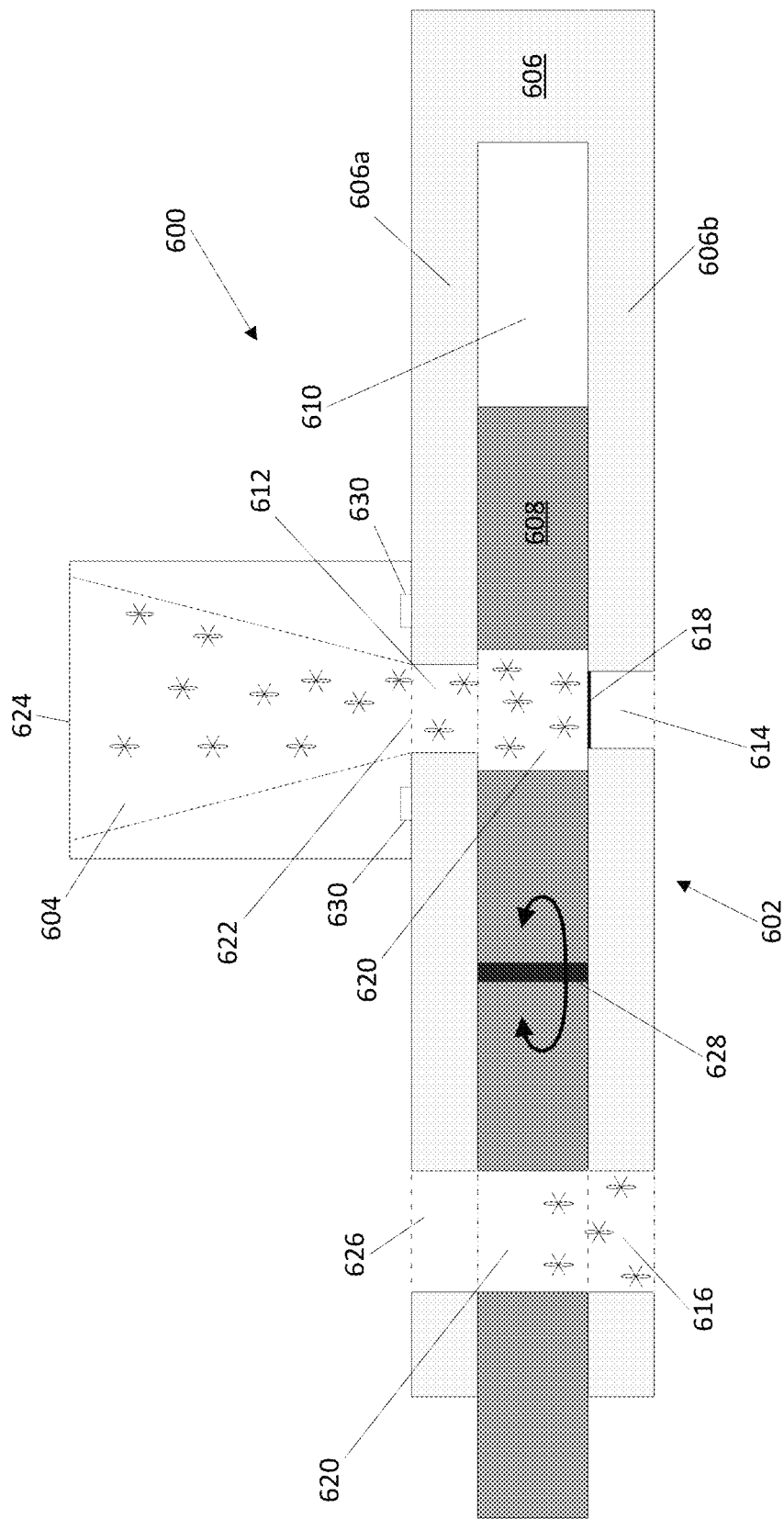

The dispenser assembly 102 includes a frame 106 and a moveable member 108 that translates within a pathway 110 defined in the frame. The frame 106 has a first surface 106a and a second surface 106b where the second surface 106b is located opposite the first surface 106a. In some examples, the first surface 106a and the second surface 106b form a top surface and a bottom surface of the frame 106. The first surface 106a may be connected to the second surface 106b at a single location, e.g., as shown in FIG. 6, or at multiple locations, e.g., as shown in FIGS. 1-3, which may form a side piece or side pieces of the frame 106. Additionally, the first surface 106a may be completely separate from the second surface 106b. In some examples, the frame is defined by a single piece of material that has been molded, extruded, machined, etc.

In this example, the frame 106 defines a pathway 110 between the first surface 106a and the second surface 106b and several openings, which include an inlet opening 112, a drain opening 114, and an output opening 116. The inlet opening 112 is defined in the first surface 106a, while the drain opening 114 and the output opening 116 are defined in the second surface 106b. The inlet opening 112, the drain opening 114, and the output opening 116 all provide access to the pathway 110 through the frame 106. In this example, the inlet opening 112 and the drain opening 114 are aligned across the pathway 110. In other examples, however, the inlet opening 112 and the drain opening 114 may be misaligned across the pathway 110 or not aligned at all. Such configurations may provide an alternate way to pre-define the bore 120 to hold a fixed number of pupae and an amount of liquid. Additionally, in this example, the first surface 106a defines a rinse opening 126 that aligns with the output opening 116, though the rinse opening 126 may be positioned to only partially align with the output opening 116.

In this example, the frame 106 also includes a filter 118 that overlays the drain opening 114 to allow water to exit the bore 120, while retaining the pupae. The filter 118, according to different examples, may be permanently coupled to the drain opening 114, removably coupled to the drain opening 114, pivotally coupled to the drain opening 114, or coupled to the drain opening 114 in any other suitable manner. Additionally, the filter 118 may be placed in or over the drain opening 114 without being physically coupled to the drain opening 114 at all. The filter 118 may be made from a mesh material or any other suitable material capable of draining a liquid while catching the insect pupae.

The pathway 110 is sized to fit the moveable member 108 while permitting the moveable member 108 to move along the pathway 110. In this example, the moveable member 108 is a sliding block. However, the moveable member 108 may be any suitable shape for moving through the pathway 110.

The moveable member 108 defines at least one bore 120 that is oriented perpendicular to the pathway 110. The bore 120 extends through the entire height of the moveable member 108. In some examples, the bore 120 may define any suitable volume to permit the dosing of the insect pupae. For example, the bore 120 may define a volume of five milliliters, ten milliliters, or fifteen milliliters. As such, the bore 120 will hold a predetermined number of insect pupae based on the volume of the bore 120. Additionally, the bore 120 may be any suitable shape for collecting a dose of pupae including cylindrical, rectangular, pyramidal, etc.

The moveable member 108 may translate between a first position and a second position in order to create a dosing of the pupae. When the moveable member 108 is in the first position, as is shown in FIG. 1, the bore 120 is aligned with the inlet opening 112. When the moveable member 108 is in the second position, as is shown in FIG. 2, the bore 120 is aligned with the output opening 116.

Referring now to FIG. 2, FIG. 2 shows an example device 200 for dispensing insect pupae. In this example, the device 200 includes similar elements, such as a dispenser assembly 202 that includes a frame 206 and a moveable member 208, and a reservoir container 204, as described above in relation to FIG. 1. Here, the insect pupae have collected and been contained in the bore 220 until the pupae fill substantially the entire volume of the bore 220. The moveable member 208 has moved to the second position so that the device 200 may output the pupae through the output opening 216. In some examples, when the moveable member 208 is in the second position, the solid portion of the moveable member 208 blocks the inlet opening 212 to prevent the mixture from flowing out of the reservoir container 204, such as is shown in FIG. 2.

Referring back to FIG. 1, the bore 120 is be aligned with both the inlet opening 112 and the drain opening 114 when the moveable member 108 is in the first position. Additionally, the moveable member 108 may be configured to translate between additional positions besides the first position and the second position, e.g., a third position, a fourth position, etc. For example, if the drain opening 114 is not aligned with the inlet opening 112, and instead is defined in the second surface 106*b* at a third position between the inlet opening 112 and the output opening 116, the moveable member 108 stops at the third position so that the bore 120 is aligned with the drain opening 114 to drain liquid from the bore 120 before proceeding to align with the output opening 116.

The dispenser assembly 102 also includes an actuator 128 that causes the moveable member 108 to move within the pathway 110. In some examples, the actuator 128 may be a hydraulic actuator, a pneumatic actuator, an electrical actuator, or any other suitable actuator that is capable of causing the moveable member 108 to move. In some examples, the actuator 128 may be coupled to the moveable member 108. For example, the actuator 128 may be screwed to the moveable member 108, bolted to the moveable member 108, adhered to the moveable member 108, or coupled to the actuator 128 using any other suitable attachment means.

In this example, the reservoir container 104 is coupled to the first surface 106*a* of the dispenser assembly 102. In some examples, the reservoir container 104 may be coupled to only the first surface 106*a*, to only the second surface 106*b*, or to both the first surface 106*a* and 106*b*. The reservoir container 104 is removably coupled to the dispenser assembly 102 using at least one detachable connector 130 such as a magnet, a screw, a bolt, a clamp, a snap-fit design, a friction-fit design, or any other suitable means for removably attaching the reservoir container 104 to the dispenser assembly 102. By removably attaching the reservoir container 104 to the dispenser assembly 102, a user may easily remove the reservoir container 104 from the dispenser assembly 102 in order to clean or replace the reservoir container 104. In some examples, the reservoir container 104 may be permanently coupled to the dispenser assembly 102. For example, the reservoir container 104 may be formed with the dispenser assembly 102 from a single piece of material.

In some examples, the reservoir container 104 also defines a dispensing opening 122 located at a first end of the reservoir container 104 and an intake opening 124. The dispensing opening 122 is aligned with the inlet opening 112. In this example, the intake opening 124 is located at an end of the reservoir container 104 opposite the first end; however, the intake opening 124 may be located at any end of the reservoir container 104. The reservoir container 104 is shaped to guide the pupae and the liquid towards the dispensing opening 122. For example, the reservoir container 104 may be shaped as a funnel, as may be seen in FIG. 2, as an inverted trapezoid, as may be seen in FIG. 1, as a ramp, or as any other suitable shape that is able to assist in guiding the pupae and the liquid to the dispensing opening 122.

In some examples, the device 100 is part of a system that incorporates various other features into the device 100. For example, the device 100 may be positioned so that the mixture is dispensed into the reservoir container 104 via a pipe and/or so that the insect pupae are output through the output opening and into a pipe, as is discussed below in reference to FIG. 3.

Additionally, various rinsing mechanisms may be incorporated into the system to help with cleaning the device 100 or dosing the pupae. The rinsing mechanisms may use a liquid, e.g., water or pressurized water, or a gas, e.g. air or pressurized air, to remove pupae or debris from various elements of the device 100. In some examples, the rinsing mechanisms may include hoses, nozzles, fans, pumps, or any other suitable device capable of outputting the water or air used to rinse the device 100.

For example, a container rinsing mechanism 138 is permanently or removably attached to the reservoir container 104. However, in some examples, the container rinsing mechanism 138 may be positioned separate from the reservoir container 104. The container rinsing mechanism 138, such as a spout, spigot, nozzle, etc. may receive and spray water or blow air from a source into the reservoir container 104 to rinse and assist in guiding the pupae towards the dispensing opening 122.

In this example, a filter rinsing mechanism 140 is positioned adjacent to the drain opening 114 so that the filter rinsing mechanism 140, such as a spout, spigot, nozzle, etc. may receive and spray water or blow air from a source through the filter 118 in order to rinse the filter 118 and remove any pupae or debris that may be stuck in the filter 118. The filter rinsing mechanism 140 may be used when the moveable member 108 is not in the first position or when there is no pupae or liquid in the reservoir container 104. In this example, the output opening rinsing mechanism 142 is positioned adjacent to or above the rinse opening 126 so that the output opening rinsing mechanism 142 such as a spout, spigot, nozzle, etc. may receive and spray water or blow air from a source through the bore 120 when the moveable member 108 is in the second position to assist with outputting the pupae from the bore 120 through the output opening 116. Additionally, the output opening rinsing mechanism 142 may be used while the moveable member 108 is not in the second position in order to clean the output opening of any debris or remaining pupae.

Referring now to FIG. 3, FIG. 3 shows another example device 300 for dispensing insect pupae. In this example, the device 300 includes the same features as were discussed above in reference to FIG. 1. The device 300 includes a dispenser assembly 302 that includes a frame 306 and a moveable member 308, a reservoir container 304, and an actuator 328. In this example, the device 300 includes features in addition to those shown in FIG. 1 to assist with dispensing insect pupae. Some of these features include, for example, an intake pipe 332 and an output pipe 334. The intake pipe 332 is positioned to dispense the mixture of the insect pupae and the liquid into the reservoir container 304. In some examples, the intake pipe 332 may be coupled to the reservoir container 304 or may be positioned adjacent to the reservoir container 304. While the intake pipe 332 is shown in FIG. 3 as positioned above the reservoir container 304, the intake pipe 332 may be positioned along any edge of the reservoir container 304. In other examples, the intake pipe 332 may be coupled directly to the first surface 306a and aligned with the inlet opening 312.

The output pipe 334 is positioned to accept the insect pupae that are dispensed from the bore 320 through the output opening 316. In some examples, the output pipe 334 may be coupled to second surface 306b of the frame 306 or may be positioned adjacent to the second surface 206b. The addition of the intake pipe 332 and/or the output pipe 334 enables the device 300 to be incorporated into a partially or fully automated insect mass rearing system. For example, the intake pipe 332 may carry the mixture of insect pupae and liquid from an upstream collection area to the device 300 without requiring a user to manually dispense the mixture into the reservoir container 304. The output pipe 334 may then carry the dosed pupae on to another area such as a sex sorting or mating location where specific, known quantities of insect pupae are required to make devices at those locations function properly.

In this example, the device 300 includes and/or is controlled by a computing device 336 communicatively coupled to the actuator 328, where the computing device 336 may control various features of the device 300. For example, the computing device 336 may control the actuator 328 that moves moveable member 308 between positions. In some examples, the computing device 336 may be communicatively coupled to the actuator 328 via a wired interface 338, such as Ethernet, USB, IEEE 1394, or a wireless interface, such as IEEE 802.11, Bluetooth, or radio interfaces for accessing cellular telephone networks (e.g., transceiver/antenna for accessing a CDMA, GSM, UMTS, or other mobile communications network(s)). While FIG. 3 only depicts a single computing device 336, it should be appreciated that multiple computing devices 336 may be employed to apportion various processing tasks. Thus, some examples may split processing amongst multiple computing devices 336 to distribute processing requirements. In some examples, the computing device 336 may be integrated into the actuator 328, coupled to the device 300, or completely separate from the device 300. In some examples, a single computing device may control multiple dispensing devices 300. Further details relating to specifics of the computing device 336 are discussed below in relation to FIG. 9.

Figure 4:
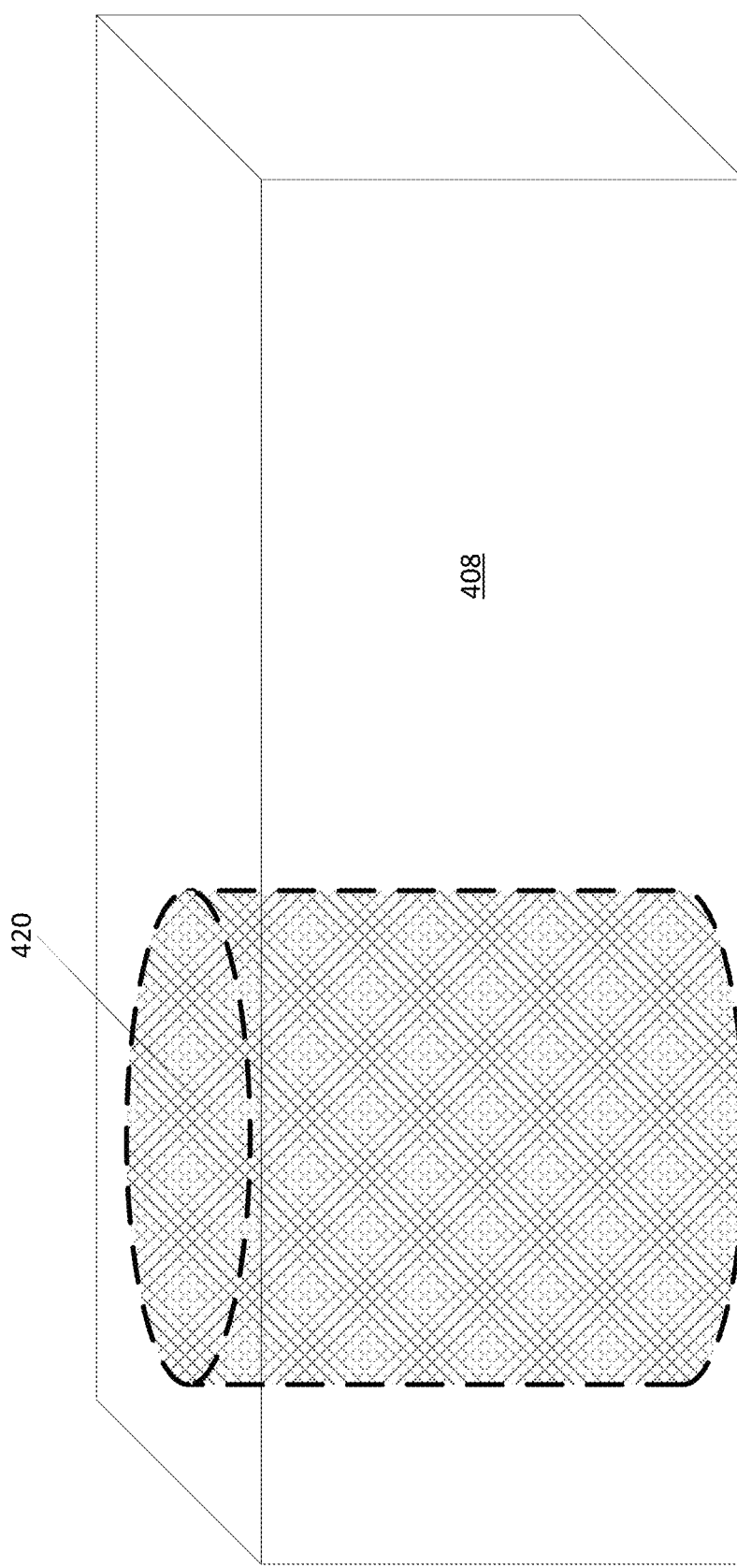

Referring now to FIG. 4, FIG. 4 shows another example of the moveable member 408 that may be included in the example device 400 for dispensing insect pupae. In this example, the moveable member 408 includes the same features as were discussed above in reference to FIG. 1. For example, the moveable member 408 defines a bore 420 extending from a first surface of the moveable member 408 to a second surface of the moveable member 408. Additionally in this example, the bore 420 includes at least one wall made out of the same material (e.g., mesh) as the filter 118 described in FIG. 1. Including mesh walls for the bore 420 may be beneficial in some examples because the greater the surface area of the bore that is made of mesh, the more accurate the count and measurement of the insect pupae may be. This is because the liquid of the mixture may be output through the entire height of the mesh wall even as the pupae begin to clog the lower portion of the mesh wall.

Figure 5:
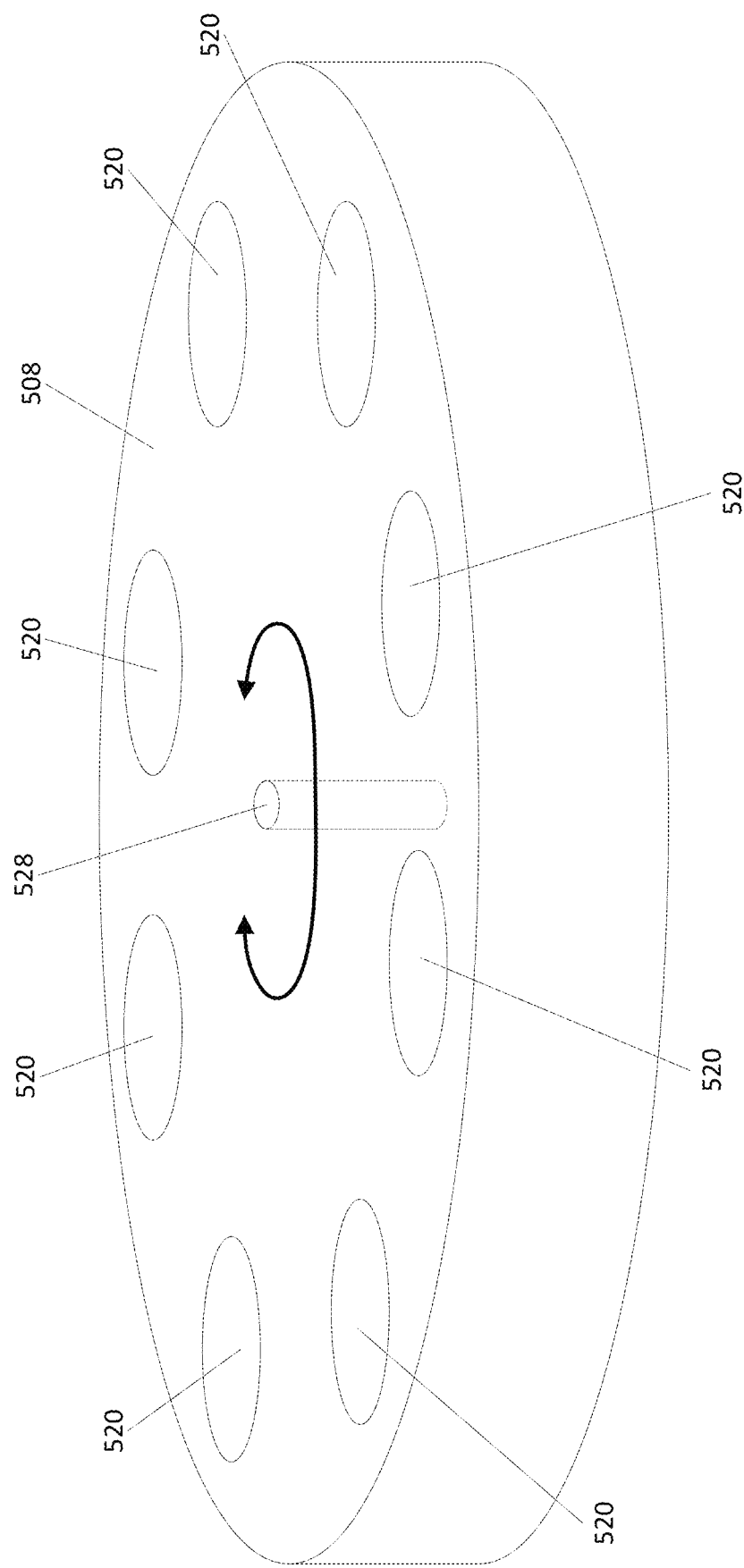

Referring now to FIG. 5, FIG. 5 shows another example of the moveable member 508 that may be included in the example device 500 for measuring and dispensing insect pupae. In this example, the moveable member 508 includes the same features as were discussed above in reference to FIG. 1. Here, the moveable member 508 is shaped as a rotatable disc. The disc shaped moveable member 508 includes at least one bore 520. The at least one bore 520 may be made of solid walls or may be made of mesh walls as described above in reference to FIG. 4. In some examples, the actuator 528 may be coupled to the moveable member 508. For example, the actuator 528 may be coupled to or embedded into a central location of the disc shaped moveable member 508, as is shown in FIG. 5. In other examples, the actuator 528 may be coupled to an outer surface of the disc shaped moveable member 508.

Referring now to FIG. 6, FIG. 6 shows another example device 600 for measuring and dispensing insect pupae. In this example, the device 600 includes similar features as were discussed above in reference to FIG. 1. The device 600 includes a dispenser assembly 602 that includes a frame 606 and a moveable member 608, a reservoir container 604, and an actuator 628. Here, the moveable member 608 is shaped as a rotatable disc and defines at least two bores 620 as described above in reference to FIG. 5 and the first surface 606a and the second surface 606b are only connected at a single location. The actuator 628 is coupled to an interior location in the moveable member 608 and causes the disc shaped moveable member 608 to rotate and move within the pathway 610. The bores 620 may be distributed around the disc shaped moveable member 608 so that a first bore 620 is be aligned with the inlet opening 612 and the drain opening 614 at the same time that a second bore 620 is aligned with the output opening 616. This allows for the simultaneous straining of the mixture in the first bore 620 and outputting of the strained pupae from the second bore 620, which results in a faster dosing of the pupae. In some examples, there may be multiple sets of reservoir containers 604, filters 618, and openings 612, 614, 616, and 622 that allows for simultaneous dosing to occur in a single device 600.

In some examples, the moveable member 608 may be removed from the device 600 and a second moveable member 608 may be interchangeable with the removed moveable member 608. The two moveable members 608 may be different shapes or have different sized bores. For example, the disc shaped moveable member 608 may be interchangeable with the sliding block shaped moveable member 108 discussed above in reference to FIG. 1. Interchanging the moveable member 608 with a second moveable member 608 of a different shape may include interchanging the actuator 628 used to move the moveable member 608 because the actuator 628 used to move the disc shaped moveable member 608 may be a different type of actuator 628 than the actuator 128 used to move the sliding block shaped moveable member 108. Additionally, the moveable member 608 may be interchangeable with a second moveable member 680 that includes at least one different sized bore 620. Having interchangeable moveable members 608 with different sized bores 620 permits a user to adjust the doses of the insect pupae being created by the device 600.

Figure 7:
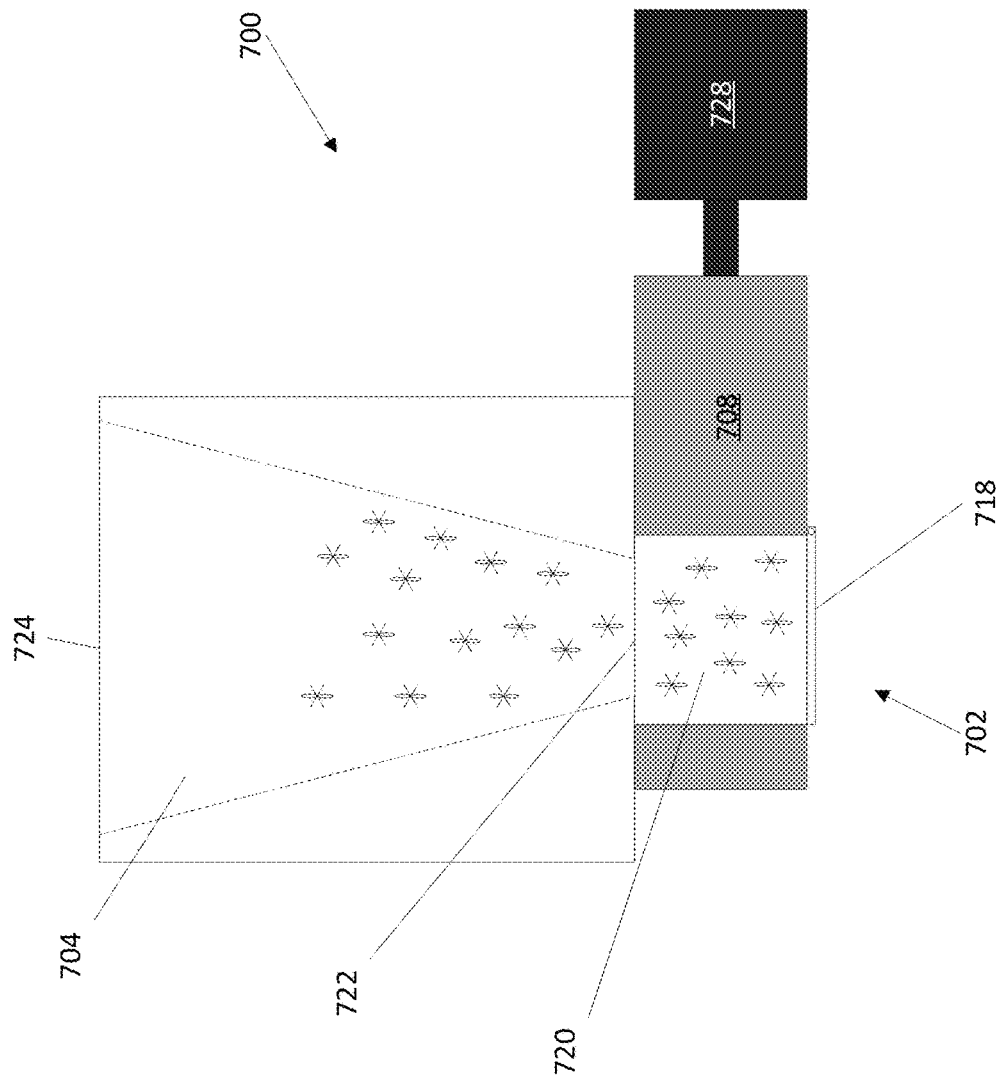

Referring now to FIG. 7, FIG. 7 shows another example device 700 for dispensing insect pupae. In the example shown in FIG. 7, the device 700 includes similar features as were discussed above in reference to FIG. 1. For example, the device 700 includes a dispenser assembly 702 that includes a moveable member 708, a reservoir container 704, and an actuator 728. However, here, the reservoir container 704 is coupled to or positioned adjacent to the moveable member 708. Thus, the mixture of the insect pupae and the liquid flow directly from the reservoir container 704, through the dispensing opening 722 in the reservoir container 704, and into the bore 720. The filter 718 is pivotally coupled to the moveable member 708 and capable of controlling when the insect pupae are contained in the bore 720 and when the pupae are released from the bore 720.

For example, when the moveable member 708 is in the first position (the bore 720 is aligned with the dispensing opening 722), the filter 718 will completely cover the lower portion of the bore 720 in order to permit the liquid to be output through the filter 718 while containing the pupae in the bore 720. When the moveable member 708 is in the second position (i.e., the solid portion of the moveable member 708 is aligned with the dispensing opening 722), the filter 718 may rotate so that the pupae may be output from the bore 720. When the filter 718 is not covering the lower portion of the bore 720 while the moveable member 708 is in the second position, either gravity or the use of water or air will cause the pupae to slide out of the bore 720 and into a container, an output pipe, etc.

Figure 8:
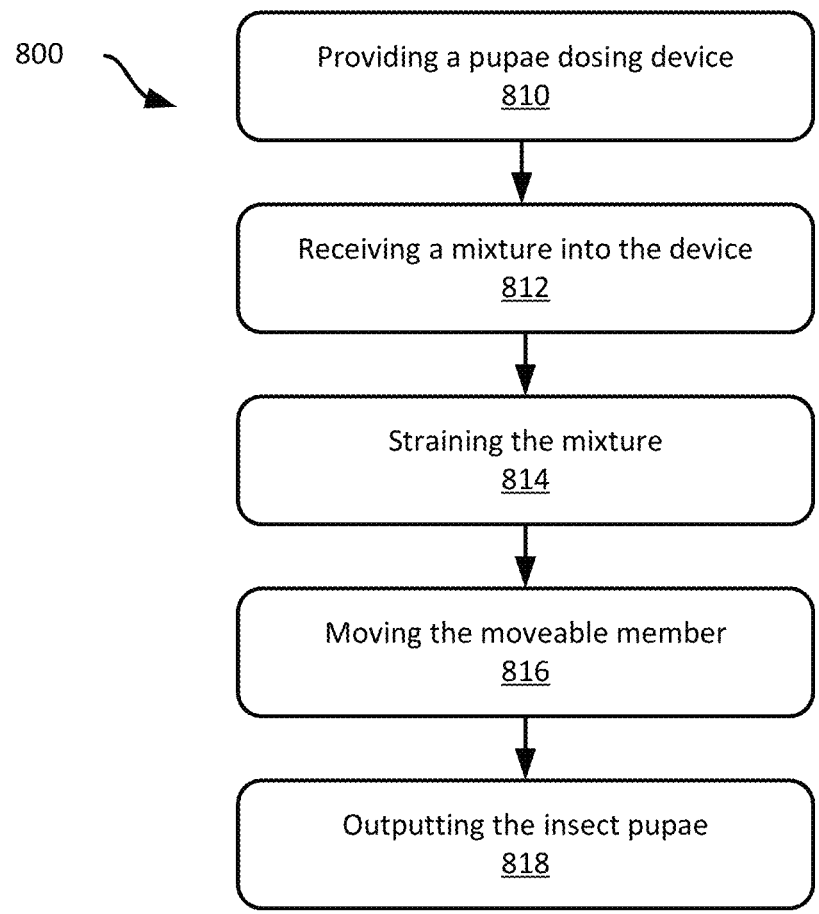
FIG. 8 shows a flowchart for an example method for dispensing insect pupae according to this disclosure.

Referring now to FIG. 8, FIG. 8 shows an example method 800 for dispensing insect pupae according to this disclosure. The example method 800 will be discussed with respect to the device 100 shown in FIG. 1. However, it should be appreciated that any suitable system for dispensing insect pupae may be employed, such as that shown in FIGS. 2-7.

At block 810, a device 100 for dispensing insect pupae is provided. Here, the device 100 includes a dispenser assembly 102, which includes a frame 106 and a moveable member 108 defining at least one bore 120, a reservoir container 104, and an actuator 128 as discussed above. The frame 106 has a first surface 106a and a second surface 106b opposite the first surface that define a pathway 110 where the moveable member 108 is located and may move through. The frame 106 defines various openings, including an inlet opening 112, a drain opening 114, an output opening 116, and a rinse opening 126, in the first surface 106a and the second surface 106b that provide access to the pathway 110. The frame may also include a filter 118 that is positioned to overlay the drain opening 114.

At block 812, a mixture of insect pupae and a liquid, such as water, is received into the reservoir container 104 of the device 100. In some examples, the mixture may be received into the reservoir container 104 from a user manually dispensing the mixture into the reservoir container 104. In other examples, the mixture may be received into the reservoir container 104 from a pipe, such as the intake pipe 332 discussed above in reference to FIG. 3 positioned to dispense the mixture directly into the reservoir container 104, or any other suitable type of upstream source that does not require manual action by a user.

At block 814, the mixture is strained using the filter 118 that overlays the drain opening 114. After the mixture is received into the reservoir container 104, the mixture is guided toward and through the dispensing opening 122 and the inlet opening 112 until the mixture reaches the bore 120 due to the shape of the reservoir container 104 and the gravitational forces acting on the mixture. Additionally, the reservoir container 104 may be rinsed with a liquid or gas, as discussed above in reference to FIG. 1, to assist with guiding the mixture towards the bore 120. In some examples, the bore 120 is not aligned with both the inlet opening 112 and the drain opening 114 at the same time. Instead the mixture flows into the bore 120 and the moveable member translates through the pathway 110 so that the bore 120 is aligned with the drain opening 114 and the filter 118 to strain the mixture.

In some examples, the straining of the mixture occurs when the liquid is output through the filter 118 overlaying the drain opening 114 while the plurality of pupae are contained in the bore. The mesh material that the filter 118 is made out of is designed to permit liquid to pass through the openings in the mesh while holding the pupae in the bore 120. As more of the liquid is output through the filter 118, more pupae will fill the bore 120 until the bore 120 reaches a point of saturation where the pupae occupy substantially the entire volume of the bore 120.

At block 816, the moveable member 108 is moved from a first position to a second position. In some examples, the moveable member 108 is moved using an actuator 128. As discussed above, the actuator may be coupled to the moveable member 108 or positioned adjacent to the moveable member 108 and may take any suitable form that is capable of causing the moveable member 108 to move (e.g., a hydraulic actuator, a pneumatic actuator, etc.). Additionally, the computing device 336, as discussed in FIG. 3, may be used to activate the actuator 128 and move the moveable member 108. While the computing device 336 is discussed in relation to the linear actuator 328 in FIG. 3, the computing device 336 may be used to activate any actuator incorporated into the device 100, including the disc shaped moveable member 508, 608 discussed in relation to FIGS. 5 and 6. In other examples, the moveable member 108 may be moved manually.

As discussed above, the moveable member 108 is in the first position when the bore 120 is aligned with the inlet opening 112. This alignment permits the mixture to flow from the reservoir container 104 into the bore 120. Here, the bore 120 is also aligned with the drain opening 114 in the first position, which permits the liquid to be output through the filter 118 overlaying the drain opening 114 at the same time as more of the mixture is flowing into the bore 120. However, in some embodiments, the drain opening 114 may be misaligned or not aligned at all with the drain opening 114.

When the moveable member 108 is in the second position, the bore 120 is aligned with the output opening 116 and the inlet opening 112 is blocked by a solid portion of the moveable member 108. This solid portion prevents any more of the mixture from flowing out of the reservoir container 104 until to bore 120 is once again positioned underneath the inlet opening 112.

In other examples, there may be no inlet opening 112 or drain opening 114 in the device, as is described above in reference to FIG. 7. Thus, the moveable member 108 is in the first position when the bore 120 is aligned with the dispensing opening 722 and is in the second position when the bore 120 is not aligned with the dispensing opening 722 such that the dispensing opening 722 is blocked by a solid portion of the moveable member 108.

At block 818, the plurality of insect pupae contained in the bore 120 are output from the bore 120 through the output opening 116. In some examples, the insect pupae may be output solely due to the gravitational forces acting on them. In other examples, a liquid, such as water, may be introduced to rinse the bore 120 to ensure that all the pupae are output from the bore.

Figure 9:
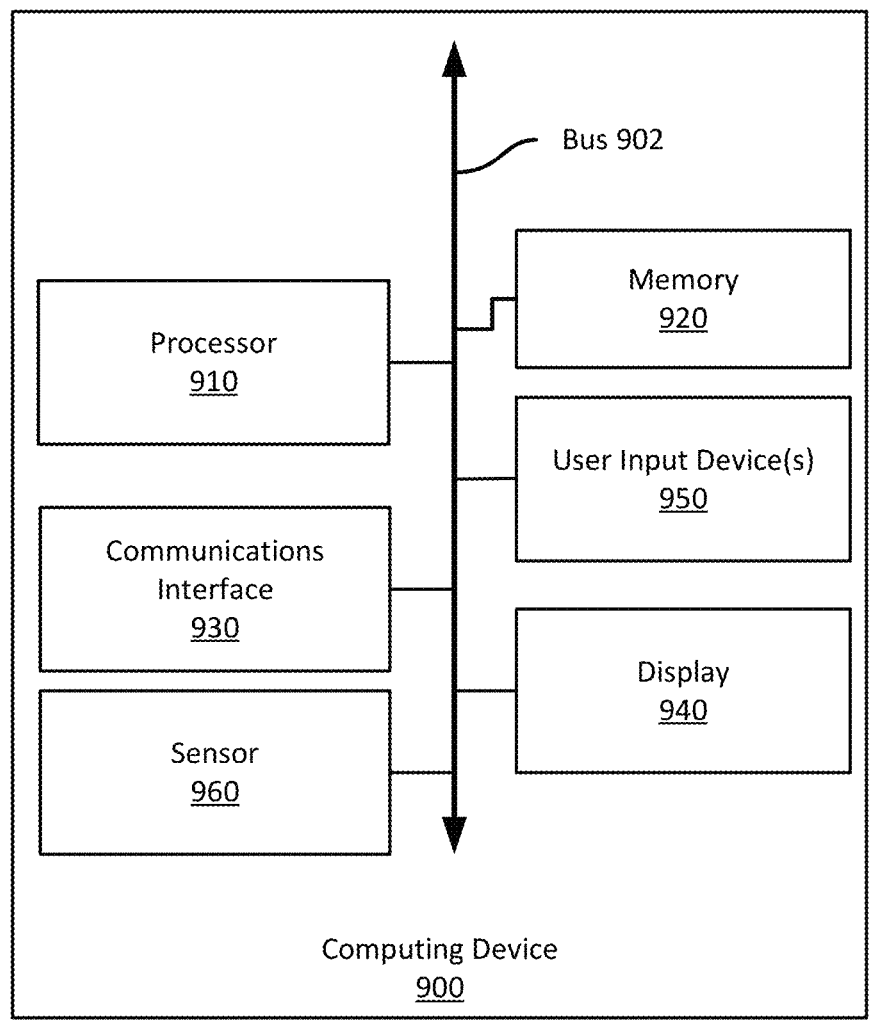
FIG. 9 shows an example computing device for dispensing insect pupae according to this disclosure.

Referring now to FIG. 9, FIG. 9 shows an example computing device 900 suitable for use in example devices or methods for dispensing insect pupae according to this disclosure. The example computing device 900 includes a processor 910 which is in communication with the memory 920 and other components of the computing device 900 using one or more communications buses 902. The processor 910 executes processor-executable instructions stored in the memory 920 to assist with dispensing insect pupae, such as instructions for part or all of the example method 800 described above with respect to FIG. 8.

In some examples, the processor 910 is part of a computerized control system for the device 100. The processor 910 may receive an actuator signal from the actuator 128 and determine a current position of the moveable member 108 based on the actuator signal. For example, the actuator signal may indicate that the actuator 128 is in a first position, a second position, or any other position. In other examples, the processor 910 may receive a sensor signal from a sensor 960 and determine a current position of the moveable member 108 based on the sensor signal. While the sensor 960 is shown as an integral element of computing device 900, the sensor 960 may be separate from and communicatively coupled to the computing device 900. The processor 910 may then transmit a movement signal to the actuator 128 based on the determined current position and the actuator 128 may be configured to move based on the movement signal.

The computing device 900, in this example, also includes one or more user input devices 950, such as a keyboard, mouse, touchscreen, microphone, etc., to accept user input. The computing device 900 also includes a display 940 to provide visual output to a user.

The computing device 900 also includes a communications interface 930. In some examples, the communications interface 930 may enable communications using one or more networks, including a local area network ("LAN"); wide area network ("WAN"), such as the Internet; metropolitan area network ("MAN"); point-to-point or peer-to-peer connection; etc. Communication with other devices may be accomplished using any suitable networking protocol. For example, one suitable networking protocol may include the Internet Protocol ("IP"), Transmission Control Protocol ("TCP"), User Datagram Protocol ("UDP"), or combinations thereof, such as TCP/IP or UDP/IP.

While some examples of methods and devices herein are described in terms of software executing on various machines, the methods and devices may also be implemented as specifically-configured hardware, such as field-programmable gate array (FPGA) specifically to execute the various methods. For example, examples can be implemented in digital electronic circuitry, or in computer hardware, firmware, software, or in a combination thereof. In one example, a device may include a processor or processors. The processor includes a computer-readable medium, such as a random access memory (RAM) coupled to the processor. The processor executes computer-executable program instructions stored in memory, such as executing one or more computer programs. Such processors may include a microprocessor, a digital signal processor (DSP), an application-specific integrated circuit (ASIC), field programmable gate arrays (FPGAs), and state machines. Such processors may further include programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may include, or may be in communication with, media, for example computer-readable storage media, that may store instructions that, when executed by the processor, can cause the processor to perform the steps described herein as carried out, or assisted, by a processor. Examples of computer-readable media may include, but are not limited to, an electronic, optical, magnetic, or other storage device capable of providing a processor, such as the processor in a web server, with computer-readable instructions. Other examples of media include, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may include code for carrying out one or more of the methods (or parts of methods) described herein.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

That which is claimed is:

1. A device for dosing a plurality of insect pupae or insect larvae comprising:
   a dispenser assembly comprising:
      a frame having a first surface and a second surface opposite the first surface, wherein the frame defines:

a pathway to enable movement of a moveable member within the frame, an inlet opening in the first surface of the frame, the inlet opening providing access to the pathway, a drain opening in the second surface of the frame, the drain opening providing access to the pathway, wherein the frame further comprises a filter overlaying the drain opening;

an output opening in the second surface of the frame, the output opening providing access to the pathway; and a rinse opening in the first surface of the frame, the rinse opening providing access to the pathway; and the moveable member translatable within the pathway between a first position and a second position, the moveable member defining at least one bore oriented perpendicular to the pathway, wherein:

at least one of the at least one bore is aligned with the inlet opening at the first position; and at least one of the at least one bore is aligned with both the output opening and the rinse opening at the second position;

a reservoir container coupled to the dispenser assembly, the reservoir container defining a dispensing opening at a first end of the reservoir container, the dispensing opening aligned with the inlet opening of the frame.

2. The device of claim 1, wherein the at least one bore of the moveable member is aligned with both the inlet opening and the drain opening at the first position.

3. The device of claim 2, wherein the reservoir container is coupled to the first surface of the frame.

4. The device of claim 1, wherein the at least one bore is aligned with the drain opening at a third position of the moveable member between the first position and the second position.

5. The device of claim 1, wherein the reservoir container comprises a mixture of a liquid and a plurality of insect pupae or insect larvae.

6. The device of claim 1, wherein the reservoir container defines an intake opening and is shaped to guide a mixture of a liquid and the plurality of insect pupae or insect larvae to the dispensing opening and the device further comprises a pipe positioned to dispense the mixture into the reservoir container.

7. The device of claim 1, wherein the filter is configured to strain a liquid from a mixture of the liquid and a plurality of insect pupae or insect larvae through the filter and the drain opening.

8. The device of claim 1, wherein the reservoir container is shaped like a funnel.

9. The device of claim 1, wherein the reservoir container is removably coupled to the dispenser assembly using at least one of magnets, screws, bolts, clamps, a snap-fit design, or a friction-fit design.

10. The device of claim 1, wherein the moveable member is a rotatable disc that defines a plurality of bores extending through the rotatable disc.

11. The device of claim 1, wherein the moveable member is translatable using an actuator.

12. The device of claim 1, wherein the at least one bore is sized to hold a predetermined number of insect pupae or insect larvae.

13. The device of claim 1, wherein the at least one bore comprises at least one mesh wall.

14. The device of claim 1, wherein the moveable member is interchangeable with a second moveable member, wherein the at least one bore of the second moveable member is a different size than the at least one bore of the moveable member.

15. A method comprising:
providing a device comprising:
a dispenser assembly comprising:
a frame having a first surface and a second surface opposite the first surface, wherein the frame defines:
a pathway to enable movement of a moveable member within the frame,
an inlet opening in the first surface of the frame, the inlet opening providing access to the pathway, and
a drain opening in the second surface of the frame, the drain opening providing access to the pathway, wherein the frame further comprises a filter overlaying the drain opening;
the moveable member translatable within the pathway between a first position and a second position, the moveable member defining at least one bore oriented perpendicular to the pathway, wherein:
at least one of the at least one bore is aligned with the inlet opening at the first position, and
a reservoir container coupled to the dispenser assembly, the reservoir container defining a dispensing opening at a first end of the reservoir container, the dispensing opening aligned with the inlet opening of the frame;
receiving a mixture of a liquid and a plurality of insect pupae or insect larvae into the reservoir container;
straining the mixture using the filter overlaying the drain opening;
moving the moveable member between the first position and the second position using an actuator; and
outputting the plurality of insect pupae or insect larvae from the at least one bore.

16. The method of claim 15, wherein the frame further defines an output opening in the second surface of the frame, the output opening providing access to the pathway, and wherein the at least one bore is aligned with the output opening at the second position.

17. The method of claim 16, wherein outputting the plurality of insect pupae or insect larvae from the at least one bore comprises outputting the plurality of insect pupae or insect larvae through the output opening.

18. The method of claim 15, wherein receiving the mixture into the reservoir container comprises receiving the mixture from a pipe positioned to dispense the mixture into the reservoir container.

19. The method of claim 15, wherein straining the mixture using the filter overlaying the drain opening comprises:
outputting the liquid through the filter overlaying the drain opening; and
containing the plurality of insect pupae or insect larvae in the at least one bore.

20. The method of claim 15, wherein the reservoir container is shaped to guide the mixture to the dispensing opening.

21. The method of claim 20, further comprising rinsing the reservoir container with a rinsing liquid to assist with guiding the plurality of insect pupae or insect larvae toward the at least one bore.

22. The method of claim 15, further comprising removing the reservoir container from the dispenser assembly.

23. The method of claim 15, further comprising rinsing the at least one bore with a rinsing liquid to assist with outputting the plurality of insect pupae or insect larvae from the at least one bore.

24. The method of claim 15, further comprising rinsing the filter overlaying the drain opening.

25. The method of claim 15, wherein the moveable member is a rotatable disc comprising a plurality of bores, and wherein moving the moveable member between the first position and the second position comprises rotating the rotatable disc.

26. An insect pupae dosing system comprising:
a dosing device comprising:
a dispenser assembly comprising:
a frame having a first surface and a second surface opposite the first surface, wherein the frame defines:
a pathway to enable movement of a moveable member within the frame,
an inlet opening in the first surface of the frame, the inlet opening providing access to the pathway,
a drain opening in the second surface of the frame, the drain opening providing access to the pathway, wherein the frame further comprises a filter overlaying the drain opening, and
an output opening in the second surface of the frame, the output opening providing access to the pathway;
the moveable member translatable within the pathway between a first position and a second position, the moveable member defining at least one bore oriented perpendicular to the pathway, wherein:
at least one of the at least one bore is aligned with the inlet opening at the first position, and
a reservoir container coupled to the dispenser assembly, the reservoir container defining a dispensing opening at a first end of the reservoir container, the dispensing opening aligned with the inlet opening of the frame;
a mixture of a liquid and a plurality of insect pupae or insect larvae;
a pipe;
a container rinsing mechanism;
a filter rinsing mechanism; and
an output opening rinsing mechanism.

27. The system of claim 26, wherein the reservoir container is shaped to guide the mixture to the dispensing opening.

28. The system of claim 26, wherein the container rinsing mechanism is configured to rinse the reservoir container with a rinsing liquid to assist with guiding the plurality of insect pupae or insect larvae to the dispensing opening.

29. The system of claim 26, wherein the pipe is positioned to dispense the mixture into the reservoir container.

30. The system of claim 26, wherein the filter rinsing mechanism is configured to rinse the filter to remove debris obstructing the filter when the moveable member is at the second position.

31. The system of claim 26, wherein the output opening rinsing mechanism is configured to assist with guiding the insect pupae or insect larvae out of the at least one bore and through the output opening while the moveable member is at the second position.

32. The system of claim 26, wherein the output opening rinsing mechanism is configured to rinse the output opening to remove any debris while the moveable member is at the first position.

33. The system of claim 26, wherein the container rinsing mechanism, the filter rinsing mechanism, and the output opening rinsing mechanism use at least one of pressurized water or pressurized air.

34. The system of claim 26, wherein the output opening is coupled to an output pipe configured to transport a dosed amount of insect pupae or insect larvae.

35. A computerized control system comprising:
a device for dosing a plurality of insect pupae or insect larvae comprising:
a dispenser assembly comprising:
a frame having a first surface and a second surface opposite the first surface, wherein the frame defines:
a pathway to enable movement of a moveable member within the frame, an inlet opening in the first surface of the frame, the inlet opening providing access to the pathway, and
a drain opening in the second surface of the frame, the drain opening providing access to the pathway, wherein the frame further comprises a filter overlaying the drain opening; and
the moveable member translatable within the pathway between a first position and a second position, the moveable member defining at least one bore oriented perpendicular to the pathway, wherein:
at least one of the at least one bore is aligned with the inlet opening at the first position;
a reservoir container coupled to the dispenser assembly, the reservoir container defining a dispensing opening at a first end of the reservoir container, the dispensing opening aligned with the inlet opening of the frame; and
an actuator configured to move the moveable member; and
a processor configured to:
receive an actuator signal from the actuator;
determine a current position of the moveable member based on the actuator signal; and
transmit a movement signal to the actuator based on the determined current position.

* * * * *